(12) United States Patent
Hegeman et al.

(10) Patent No.: US 7,720,192 B2
(45) Date of Patent: May 18, 2010

(54) X-RAY FLUORESCENCE APPARATUS

(75) Inventors: Petra Hegeman, Borne (NL); Christian Brons, Ootmarsum (NL); Peter Brouwer, Wierden (NL)

(73) Assignee: PANalytical B.V., Almelo (NL)

( * ) Notice: Subject to any disclaimer, the term of this patent is extended or adjusted under 35 U.S.C. 154(b) by 35 days.

(21) Appl. No.: 12/080,816

(22) Filed: Apr. 4, 2008

(65) Prior Publication Data

US 2008/0310587 A1    Dec. 18, 2008

(30) Foreign Application Priority Data

Apr. 5, 2007    (EP)    .................... 07105796

(51) Int. Cl.
*G01N 23/223*    (2006.01)
(52) U.S. Cl. ............................................ 378/44
(58) Field of Classification Search ............. 378/44–48, 378/49, 50, 82
See application file for complete search history.

(56) References Cited

U.S. PATENT DOCUMENTS

| | | | | |
|---|---|---|---|---|
| 2,837,655 | A | | 6/1958 | Lang ........................... 250/52 |
| 3,790,792 | A | | 2/1974 | Ishijima ...................... 250/278 |
| 4,121,098 | A | | 10/1978 | Jagoutz et al. .............. 250/273 |
| 5,381,791 | A | * | 1/1995 | Qian ........................... 600/436 |
| 5,424,959 | A | * | 6/1995 | Reyes et al. .................. 702/28 |
| 5,481,109 | A | * | 1/1996 | Ninomiya et al. ........... 250/310 |
| 6,577,705 | B1 | * | 6/2003 | Chang et al. .................. 378/45 |
| 6,771,802 | B1 | * | 8/2004 | Patt et al. .................... 382/128 |

| | | | |
|---|---|---|---|
| 2006/0072701 | A1 | 4/2006 | van Kessel .................... 378/47 |

FOREIGN PATENT DOCUMENTS

JP    2002 365245 A    12/2002

OTHER PUBLICATIONS

European Search Report for European Application No. EP 07105796.2, Oct. 31, 2007.
Hah-Weinheimer, Hirner, Weber-Diefenbach "Grundlagen und praktische Anwendung der Röntgenfluoreszenzanalyse (RFA)" XP 002454262, pp. 33-34, 79 and 235, 1984.
Takahashi et al. "Application of X-Ray Absorption Near-Edge Structure (XANES) using Bent Crystal Analyzer to Speciation of Trace Os in Iron Meteorites" XP005257940, vol. 558, No. 1-2, pp. 332-336, Feb. 3, 2006.
Sieber et al. "Improved Determination of Cobalt in Steel by X-Ray Fluorescence Analysis" XP002454261, pp. 287-288, Oct. 1986.
The Institution of Electrical Engineers, Stevenage, GB "Recent Advances and Future of X-Ray Fluorescence Analyses" XP002454267, vol. 74, No. 4, pp. 453-461, Apr. 2005.
R. Jenkins, R.W. Gould and D Gedcke, "Quantitative X-Ray Spectrometry", R. Dekker, New York, p. 408, 1995.
2008 Internet a preprint article discovered by the EPO Search Examiner of H.P. Grnir, et al., "Resolution and efficiency of silicon draft detectors (SDD) compared with other solid state X-ray systems". XP002474812, Institut de Physique Nucléaire, Atomique et Spectroscopie, Université de Liège,pp. 1-8, 2006.

(Continued)

*Primary Examiner*—Edward J Glick
*Assistant Examiner*—Mona M Sanei
(74) *Attorney, Agent, or Firm*—Proskauer Rose LLP

(57)    ABSTRACT

An X-ray fluorescence (XRF) apparatus uses both an analyzer crystal (6) and a silicon drift detector (34). By using this combination problems of background and overlapping peaks can be mitigated.

20 Claims, 12 Drawing Sheets

OTHER PUBLICATIONS

Jagoutz, E., et al. "Vielkanal fuer die Roentgenfluoreszenzanalyse". XP009090666, Geochemistry Section, German Mineralogical Society, pp. 138-140, 1976.

Brief English summary of Jagoutz, E., et al. "Vielkanal fuer die Roentgenfluoreszenzanalyse". XP009090666, Geochemistry Section, German Mineralogical Society, pp. 138-140, 1976.

K. Weber, et al. "A Device For Coupling a Pulse Height Discriminator to a Scanning X-Ray Spectrometer" XP002052584, Journal of Scientific Instruments, Institute of Physics, vol. 41, No. 1, pp. 15-22, Jan. 1964.

European Search Report for European Application No. EP 07 10 5796.

Izumi Nakie "Recent Advances and Future of X-Ray Fluorescence Analyses". Oyo Butsuri, vol. 74, No. 4, pp. 453-461, (2005). (Partial English Translation).

Partial English translation of P. Hahn-Weinheimer, et al. "Basics and Practial Uses of X-Ray Fluorescence (XRF)." XP-002454262, (1984).

* cited by examiner

US 7,720,192 B2

X-RAY FLUORESCENCE APPARATUS

CROSS-REFERENCE TO RELATED APPLICATIONS

This application claims priority under 35 U.S.C. §119(a)-(d) or (f), or 365(b) to European Community, Application No. 07105796.2, filed Apr. 5, 2007, the entire contents of which are incorporated herein by reference.

TECHNICAL FIELD

The invention relates to X-ray fluorescence (XRF), and to an apparatus that uses XRF.

BACKGROUND

XRF is a well known technique for measuring properties of samples. A number of different configurations are known.

In wavelength dispersive XRF (WDXRF), X-rays from an X-ray source are incident onto a sample. These cause X-ray fluorescence, i.e. X-rays emitted at a range of energies that act as a signature of the sample material. In a first arrangement, illustrated in FIG. 1, X-rays are emitted by tube 2 as the source and then are incident on sample 4. The X-rays from the sample are incident on a flat analyzer crystal 6 which diffracts them according to the Bragg equation onto a detector 8. By moving the analyzer crystal 6 by angle θ and detector 8 by double the angle 2θ, the wavelength of X-rays diffracted by the flat analyzer crystal into the detector changes and so the movement of the detector allows the measurement of a range of wavelengths and hence energies. The analyzer crystal provides good discrimination between different wavelengths. The X-rays pass through parallel plate collimators 11, 13.

A variant of this arrangement uses a curved analyzer crystal 10 as illustrated in FIG. 2 in combination with a first slit 12 adjacent to the sample 4 and a second slit 14 adjacent to the detector 8. The curved analyzer crystal 10 acts as a monochromator only imaging X-rays at a particular energy passing through first slit 12 onto second slit 14.

In this approach, the curved crystal 10 provides the discrimination between different wavelengths, and hence energies. In general, a different curved analyzer crystal is used for each energy. Alternatively, the curved analyzer crystal 10 can be mounted on a goniometer and rotated in a similar manner to the approach of FIG. 1.

In order to measure at a range of energies an alternative approach known as Energy Dispersive XRF (EDXRF) may be used. In this approach, the X-rays emitted by the sample are measured directly in a detector that can measure the intensity as a function of energy. Such a detector may be, for example, a silicon drift detector that can measure at a range of energies simultaneously. The silicon drift detector avoids the need for a crystal since this would only direct one wavelength into the detector and the whole point of EDXRF is to measure multiple wavelengths. Instead, the detector is normally simply mounted directly close to the sample.

A problem that occurs in current spectrometers is the existence of a background signal in addition to the Bragg reflected signal from the sample that is intended to be measured. This is radiation from a number of sources that is picked up by the detector. The sources of background include scattering from the tube, fluorescent radiation from the sample and contamination in the optical path, the tube, the crystal, and/or the detector.

It is commonly believed that the main part of the background is the tube spectrum scattered by the sample—see for example the text book R. Jenkins, R. W. Gould and D Gedcke, "Quantitative X-Ray Spectrometry", 1995 R. Dekker, New York, page 408: "The most significant contribution to background is due to the X-ray tube spectrum scattered by the specimen . . . ".

SUMMARY OF THE INVENTION

According to the invention there is provided XRF apparatus according to claim 1.

Note that in addition to the selection of measurement energy using the configuration of sample, source, analyzer crystal and detector as in conventional WDXRF, the detector, attached measurement electronics or a computer may select an output energy window. The intensity of X-rays in the output energy window is output as the output signal.

It might at first be thought that using an energy-resolving solid state detector in combination with an analyzer crystal does not deliver any benefit, since the analyzer crystal effectively selects a particular energy and so the detector does not receive multiple energies simultaneously. The normal benefit of being able to measure such multiple energies at once is therefore not achieved.

However, the combination of crystal and energy-resolving detector does give rise to unexpected benefits.

By using a relatively high resolution energy-resolving detector in the WDXRF approach different contributions to the background can be identified and accordingly corrected for. An example is presented below demonstrating the significant improvement using the approach of the present invention.

The inventors have realised that background scattering caused by scattered fluorescent radiation from the sample is in fact highly significant. In particular, in conventional WDXRF, there are typically a number of strong X-ray fluorescence peaks emitted by the sample. Even when the analyzer crystal is not oriented at the Bragg angle, some X-rays will be scattered by the crystal, even though this is at relatively low amplitude. This is somewhat contrary to the conventional view (see above) that the X-ray tube spectrum is more important. By separating out the different contributions, an improved background correction may be made.

In particular, the processing means may be arranged to output the X-ray intensity of a peak at peak energy, by:

measuring a measured peak X-ray spectrum of the peak;

measuring the X-ray spectrum of a Bragg-reflected background peak at at least one measurement energy and corresponding output energy, both the measurement energy and output energy being spaced from the peak energy;

using the measured X-ray spectrum of the Bragg-reflected background peak to estimate the X-ray spectrum of the Bragg-reflected background peak; and outputting a corrected peak X-ray intensity of the peak by subtracting the estimated X-ray spectrum of the Bragg-reflected background peak from the measured peak X-ray spectrum.

By using an energy resolving detector, it is possible to correct for the scattered radiation background since it is at a different energy to the energy being measured. This removes this component and hence reduces the background. This makes it easier to detect small peaks in the XRF spectrum which is very useful for trace analysis.

Moreover, the use of the combination of crystal and energy-resolving detector can also deal with overlapping peaks. These may arise, for example, from crystal fluorescence, i.e. XRF in the crystal instead of the sample. For example, peaks from Na or Mg in the sample may overlap with peaks from a W/Si multilayer crystal. Alternatively, the overlapping peaks may arise from different elements in the sample. Overlapping peaks may also arise from the tube, components in the optical path such as a filter, filterwheel, collimators, crystal holder etc, or from the envelope.

BRIEF DESCRIPTION OF THE DRAWINGS

For a better understanding of the invention, embodiments will now be described with reference to the accompanying drawings, in which.

DETAILED DESCRIPTION

Figure 1:
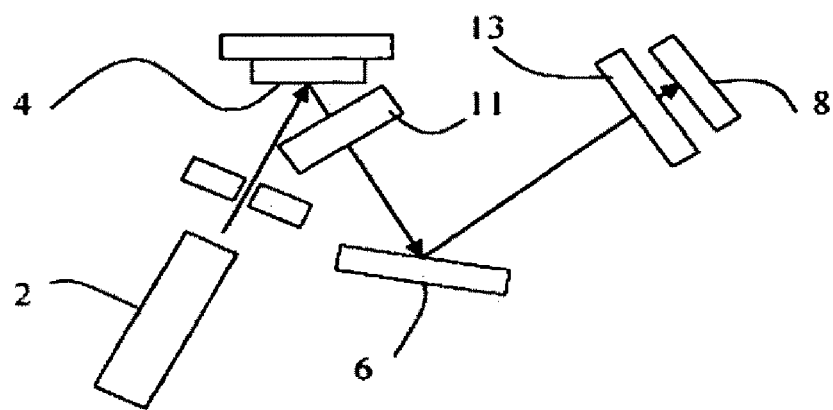
FIG. 1 illustrates a prior art WDXRF apparatus.

The Figures are schematic and not to scale. Like or similar components are given the same reference numerals in the different Figures.

Figure 3:
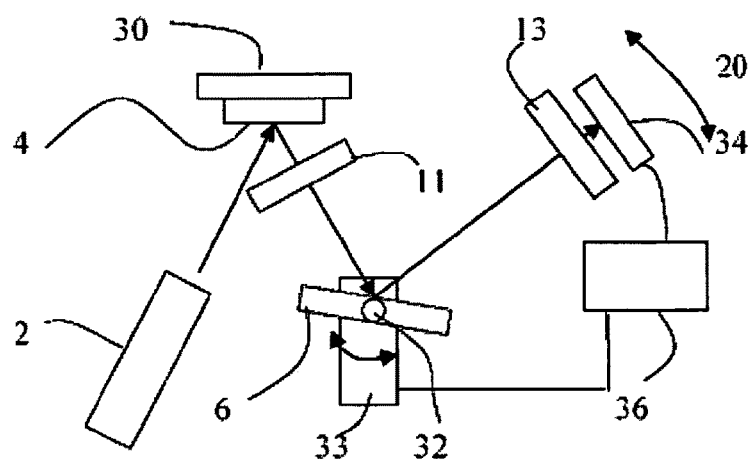
FIG. 3 shows apparatus according to a first embodiment of the invention.

Referring to FIG. 3, a WDXRF application according to the invention includes a X-ray source 2, a sample stage 30 for holding a sample 4, and a flat single analyzer crystal 6 mounted on a goniometer axis 32 for rotation about the axis by drive means 33. The analyzer crystal may be of LiF, PE, TlAP, InSb, Ge, for example or a multilayer of W/Si, Mo/$B_4$C, Ni/C, Cr/C, Fe/Sc or La/$B_4$C for example. A primary collimator 11 and a secondary collimator 13 direct X-rays from the sample to the detector, the X-rays being reflected by the analyzer crystal. Note that the collimators are shown schematically and in practice any suitable form of collimator may be used.

Unlike the arrangement of FIG. 1, the detector in this case is a silicon drift detector (SDD) 34 that measures the intensity of radiation as a function of energy.

The detector 34 and the drive means 33 are connected to control electronics 36 that may include, for example, a computer with suitable software.

Figure 4:
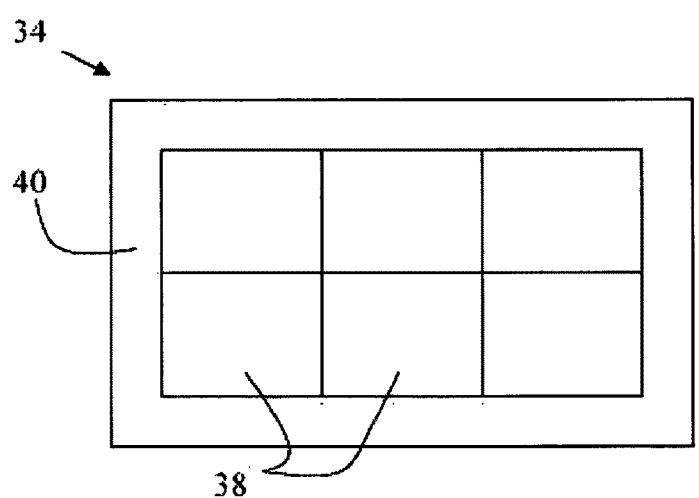
FIG. 4 shows a detector used in the apparatus of FIG. 3.

The X-ray spot size at the detector in this configuration is typically larger than a conventional silicon drift detector that may be as little as 10 mm$^2$ or even 5 mm$^2$. Accordingly, as illustrated in FIG. 4, the detector 34 is made up of a two-dimensional array of a plurality of detector elements 38 integrated on a common substrate 40. Each detector element 38 is in essence a single silicon drift detector. Alternative forms and arrangements of detector elements 38 are possible; it may even be possible to use a single segment detector, at the cost of an increased measurement time.

In use, a sample 4 is mounted on the sample stage 30 and the X-ray source 2 switched on. The crystal 6 and detector 34 are then rotated by drive means 33 under the control of the control electronics 36 about goniometer axis 32 to scan over a range of energies. The crystal 6 is rotated by angle $\theta$ and detector 34 by double the angle $2\theta$. As the scan over angles, and hence energies, takes place, the intensity of X-rays Bragg-reflected onto the detector 34 varies. The control electronics 36 select a narrow window of energy around the output energy of the Bragg reflection, and output the X-ray intensity in this window as the output intensity as a function of output energy.

Note that in this arrangement the detector 34 measures at a range of energies and the selection of the window occurs in the control electronics 36, most conveniently in software.

In one approach, as the analyzer crystal 6 is rotated, the selected output energy and the narrow window of energy around the output energy follow the measurement energy selected by the orientation of crystal, detector, and sample. Suitable sizes of the narrow window will be described below. In this way, a single graph of intensity as a function of energy is output.

In this way, a scan over energy is carried out that reduces the background, and in particular removes the contribution to background caused by scattering in the crystal of X-rays of high intensity peaks. This is of particular benefit since the remaining background may be largely a conventional background decreasing with energy and it is possible to take account of this and correct for it with suitable software. It will be appreciated that the benefit of reduction of background applies even if the background is increasing or flat.

Suitable software may be incorporated into the control electronics which may have a number of additional functions, including for example the ability to display results on a screen, print them out, or analyze them in various ways.

Figure 5:
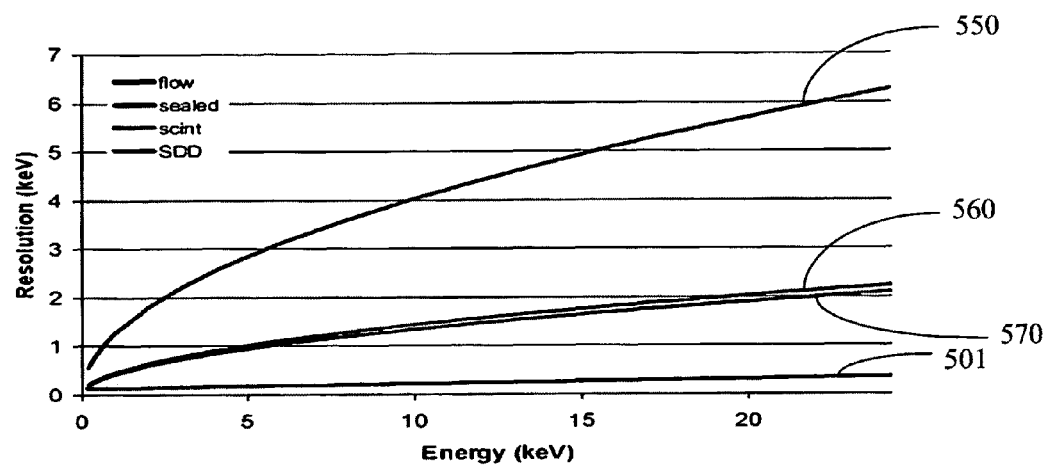
FIG. 5 shows the calculated resolution of various detectors as a function of energy.

FIG. 5 illustrates the resolution in keV as a function of energy of a SDD (lowest curve, 501) in comparison with conventional scintillator detectors (upper curve, 550), and sealed (560) and flow type (570) detectors (middle curves). The great improvement in energy resolution using an SDD detector may be seen. This improvement in resolution makes the invention possible.

Experiments were performed and results will be presented with reference to FIGS. 6 to 10. As described above, it is generally preferred to use a multisegment SDD with an increased sensitive area, resulting in more rapid measurements, in which case a smaller step size may be used, for example 0.05° to 1°. However, a multi-segment SDD was not available for these early experiments, so a single segment SDD was used instead, increasing the measurement time accordingly to compensate for the lower X-ray intensity.

The sample is ZnO which was irradiated by 60 kV X-rays. A primary collimator is present between the sample and the LiF crystal and a secondary collimator between the LiF200 crystal and the detector.

Figure 6:
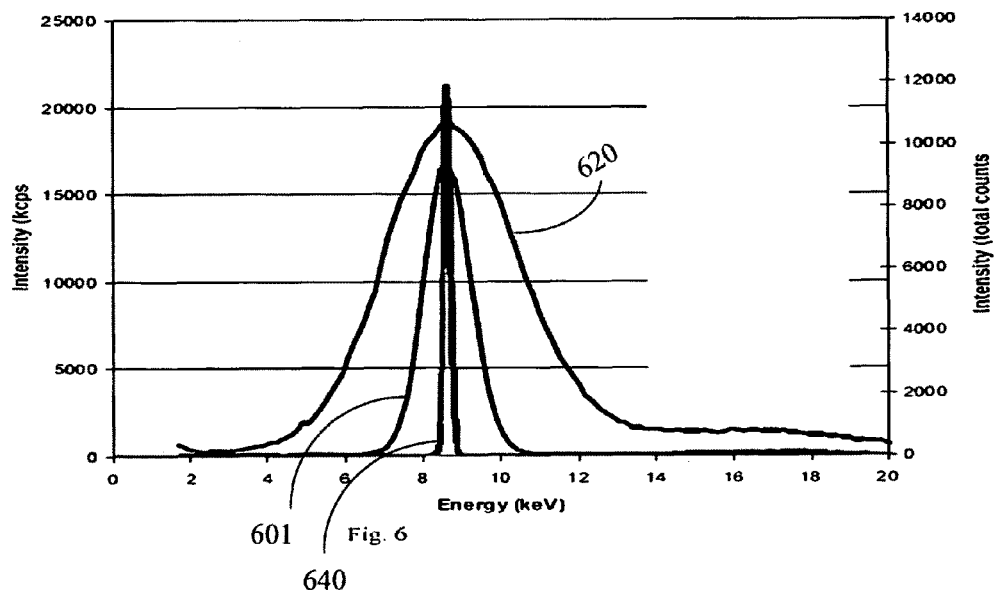
FIGS. 6 to 9 show measurements of a ZnO sample.

FIG. 6 shows the spectrum as a function of output energy measured at the Bragg angle ($2\theta=41.800°$) for Zn using three different detectors, namely a gas-filled proportional counter (middle peak, 601), a NaI scintillation counter (broad peak, 620) and an SDD (narrow peak, 640). The improved resolution of the SDD is clearly visible.

Figure 7:
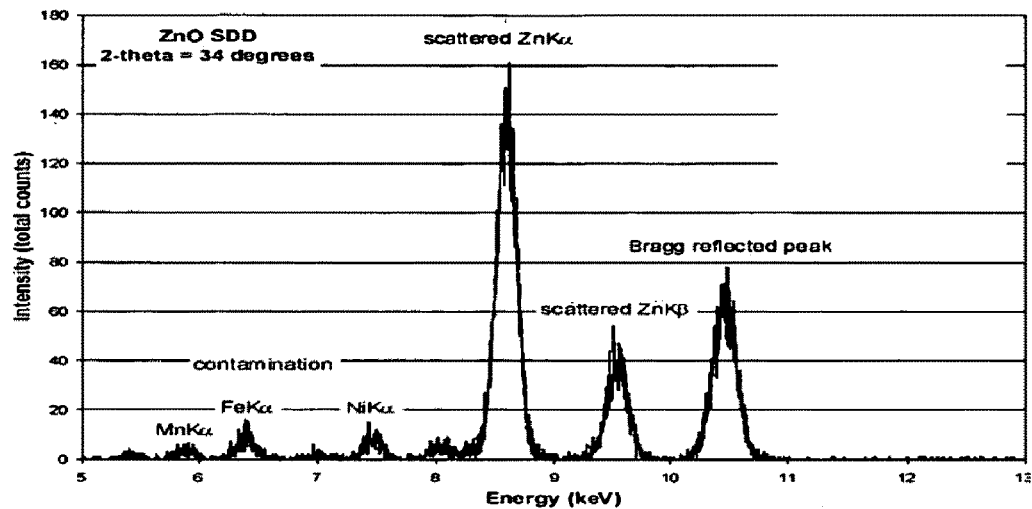

FIG. 7 shows the spectrum (as a function of output energy) measured at a fixed angle $2\theta$ of 34° (and hence fixed measurement energy) close to the ZnKα and ZnKβ peaks. In these conditions, a number of components of intensity are seen. One component is the contribution from the ZnKα peak, i.e. from ZnKα X-rays emitted from the sample. Even though the analyzer crystal is not at the correct angle to Bragg-reflect the ZnKα fluorescence onto the detector, some ZnKα X-rays nevertheless scatter onto the detector giving the largest peak seen.

A similar component is the ZnKβ peak which arises from the ZnKβ fluorescence in the same way.

The Bragg reflected peak corresponds to the X-ray radiation at the correct energy to be Bragg reflected onto the detector by the analyzer crystal 6, i.e. the measurement energy which in this case is approximately 10.5 keV. Although there is no (or very little) X-ray fluorescence at this energy, some X-rays are scattered off the sample at this energy which results in the significant peak seen.

Three smaller components are also seen. These are peaks from contamination by elements in housing of the silicon drift detector 34 namely Mn, Fe and Ni respectively.

Figure 8:
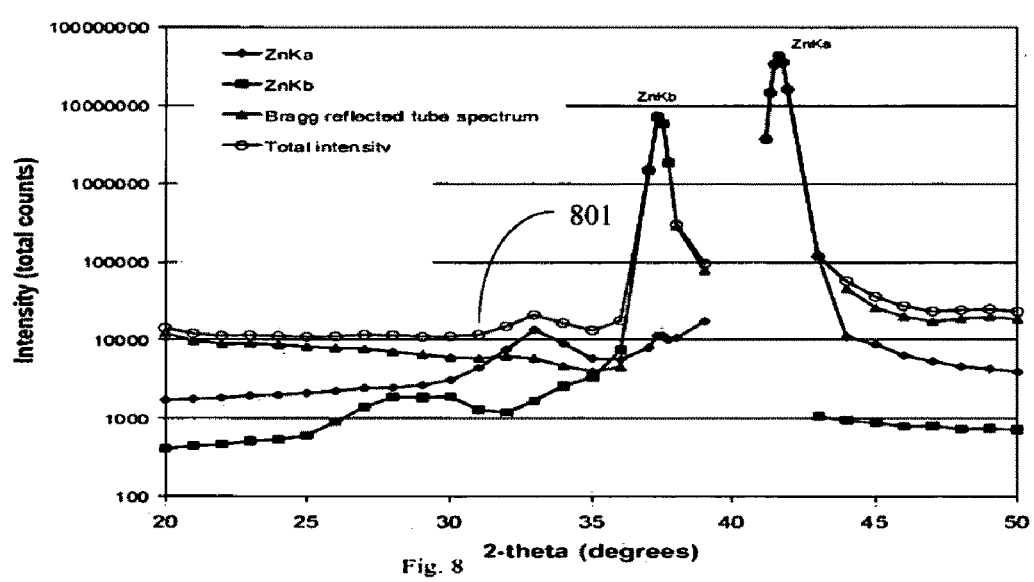

A θ-2θ scan was carried out and the results presented in FIG. 8 using a LiF200 crystal and an SDD. The step size Δ2θ is 1°. The large step size was used because of the slow measurements imposed by the use of a single segment SDD.

To check these identifications of the peaks of FIG. 7, the experiment was repeated for a number of angles 2θ. The scattered ZnKα and ZnKβ peaks, as well as the contamination peaks, remained at the same energy for different 2θ, whereas the Bragg reflected peak is at an energy that is a function of 2θ, as would be expected since the Bragg energy is a function of 2θ.

Figure 9:
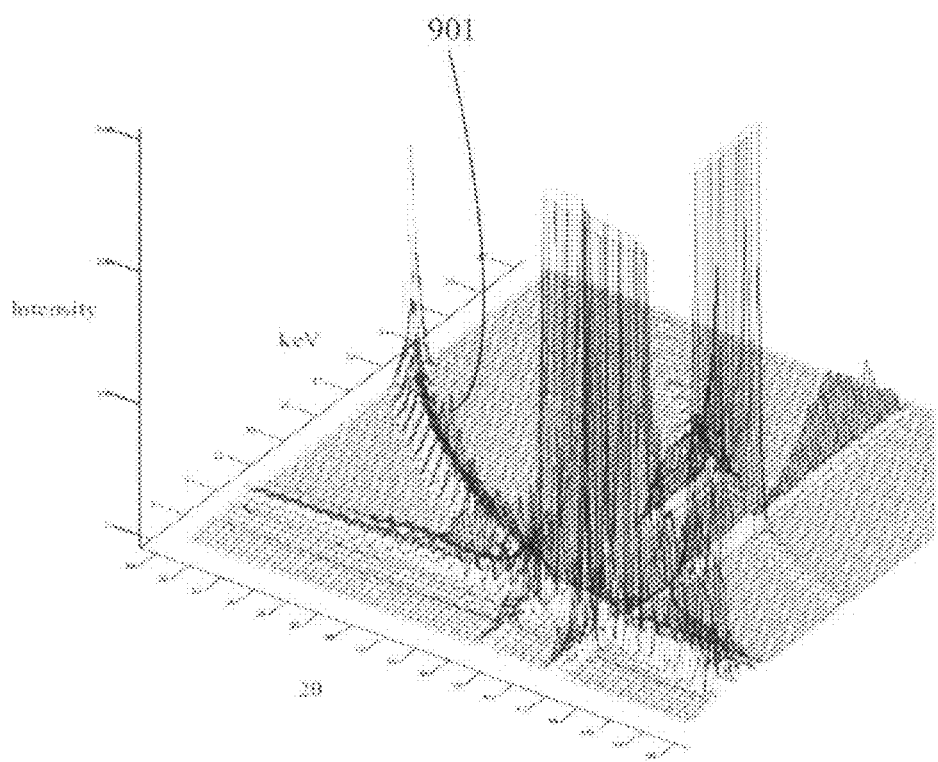

FIG. 9 shows the measured intensity in a three-dimensional plot as a function of both output energy (keV) and angle 2θ, the latter being a measure of measurement energy. The Bragg peak 901 which is the peak that varies as a function both of energy and angle can be clearly identified. Since the other contributions can be identified, their effects can be calculated and corrected for. For example, the peaks caused by scattering have constant energies at 8.63 keV for the ZnKα and 9.57 keV for the ZnKβ and at an angle 2θ of 34 degrees the Bragg reflections are a peak between 10 and 11 keV, identifying the peaks in FIG. 7.

Once the strength of the background Bragg reflected peak is known, its contribution to the intensity of the measured peak, for example the ZnKα peak, can be measured. The measured peak can then be corrected. Note in FIG. 9 (and FIG. 7) that at an angle 2θ of 34°, there is more than one component of total energy—it is only by using the approach of the invention that these can be separated and hence the background correction correctly calculated.

It will be appreciated from this graph that there are a number of ways of recording the data to carry out the background correction. One way is to record the data as a function of both output and measurement energy, as illustrated in FIG. 9, and then carry out the windowing (i.e. the application of the narrow range) and background correction in software. An alternative approach is to scan the measurement energy and output energy together and record only data in the narrow range, since the background Bragg peak is the peak at matching output and measurement energies, the curved line 901 in FIG. 9.

Returning to FIG. 8, which illustrates the background correction, this shows the total measured intensity as function of angle 2θ using a SDD detector. The total intensity—the plot 801 using circles—is made up of contributions of different energy which can be identified since the SDD measures intensity as a function of energy. The components, i.e. the ZnKα component, the ZnKβ component and the Bragg reflected component of the total intensity are identified by diamonds, squares and triangles respectively in FIG. 8.

Without using the SDD for energy dispersive WDXRF measurements it would only be possible to measure total intensity. As can be seen, by using the SDD it is possible to have a much lower background intensity by correcting for the other contributions. At an angle 2θ of 35°, for example the measured intensity of the Bragg reflected peak is a factor 3 less than the total intensity. The Bragg reflected peak is the true background.

This reduction in background is of course much more important when measuring samples with weaker peaks than the ZnO sample tested here.

In normal use, to measure a sample, all that the user has to do is to record the X-ray intensity as a function of the angle 2θ, where the X-ray intensity is measured in a narrow range of output energy around the measurement energy which depends on 2θ.

The narrow range of output energy determined by detector and processor need not be constant over energy, but may vary. Expressed in percentage terms, the narrow range may be a higher percentage of output energy at lower energies, but expressed in absolute terms, the narrow range may be a lower absolute size at lower energies. The ranges will be expressed as full width: taking the output energy as the centre of the range the range will accordingly be from output energy minus half the narrow range to the output energy plus half the narrow range.

In particular, the narrow energy range may be less than 0.4 keV for an output energy below 1 keV, less than 1 keV for an output energy from 1 keV to 5 keV, less than 2 keV for an output energy from 5 keV to 10 keV, and less than 5 keV for an output energy above 10 keV.

Narrower ranges can improve results: for example the range may be less than 0.4 keV for an output energy below 1 keV, less than 0.5 keV for an output energy from 1 keV to 5 keV, less than 1 keV for an output energy from 5 keV to 10 keV, and less than 2 keV for an output energy above 10 keV. A further improved range may be less than 0.4 keV for an output energy below 1 keV, less than 0.5 keV for an output energy from 1 keV to 5 keV, less than 0.8 keV for an output energy from 5 keV to 10 keV, and less than 1 keV for an output energy above 10 keV.

Note also that the narrow range does not need to be a step function of energy. For example, for a scan from 2 keV to 30 keV, a constant energy range of 1 keV may be used. Alternatively, a smooth function may be used. A suitable scan range might be 1 keV to 30 keV, or whatever smaller or different range would be suitable depending on the elements being measured.

Alternatively, the way of imposing the narrow range on the measured data may be to deconvolve the measured data with a narrow function.

This may in particular be done by fitting the peaks, for example to a Gaussian (Normal) curve. In this case, the narrow range of energy imposed in the method is the width of the peak, by some appropriate measure. One measure of the width of the peak is the full width of the peak at one tenth the maximum intensity (Full width at one tenth the maximum intensity—FWTM). Another measure is the standard deviation C used as a measure of the width of the peak. The peak width may be represented by a range from the peak position less 3σ to the peak position plus 3σ. For a Gaussian shape peak, these two measures are quite similar.

Using the measure of the peak width from the peak position less 3σ to the peak position plus 3σ, i.e. a full width of 6σ, the full width should be within the ranges set out above for the narrow energy range, i.e. less than 0.4 keV for an output energy below 1 keV, less than 1 keV for an output energy from 1 keV to 5 keV, less than 2 keV for an output energy from 5 keV to 10 keV, and less than 5 keV for an output energy above 10 keV. Preferably, the full width 6σ is within the narrower preferred energy ranges set out above.

Figure 10:
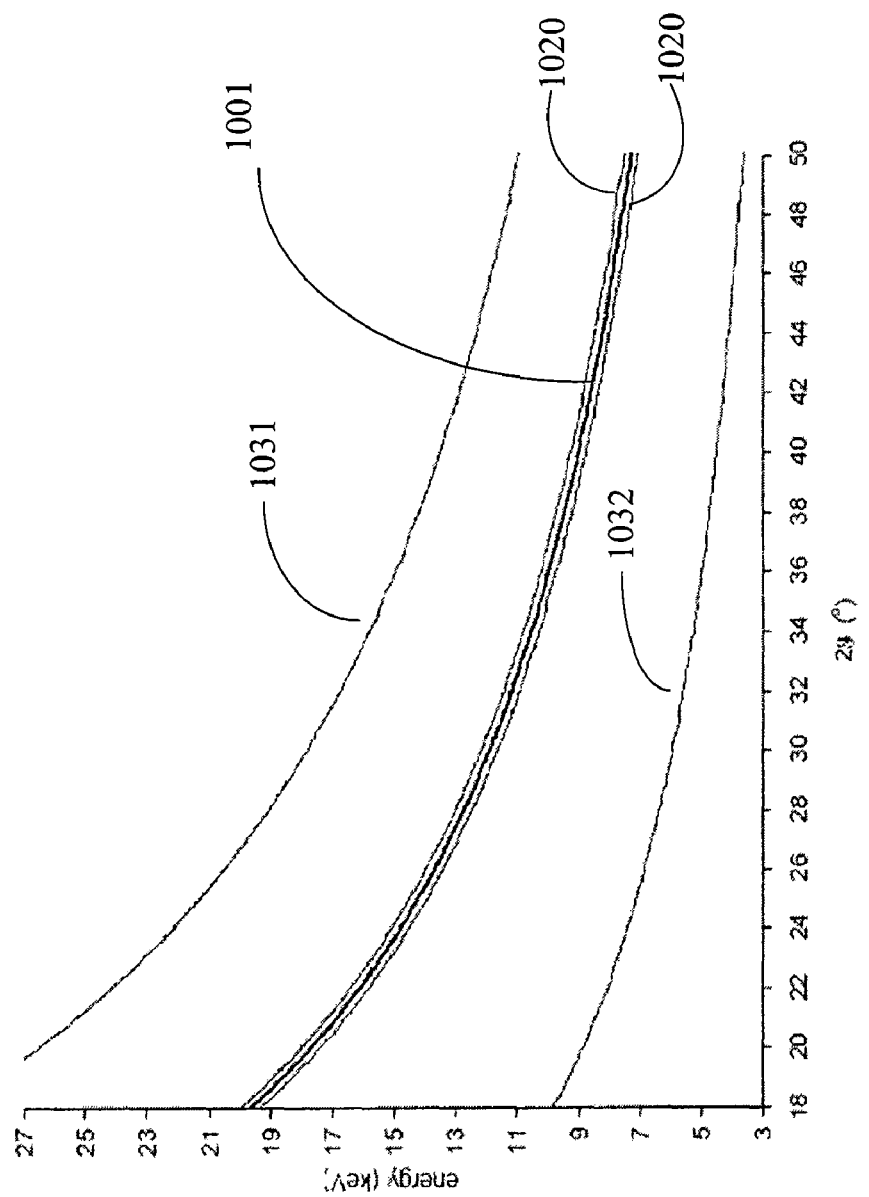
FIG. 10 shows energy ranges used in an embodiment of the invention.

FIG. 10 illustrates suitable output energy ranges. The heavy line 1001 indicates the measurement energy as a function of 2θ. The narrow window around the line 1020 indicates the narrow range of energy output in the embodiment. The broader lines 1031, 1032 are indicative of the very much broader range of energy measured in prior art WDXRF approaches.

Thus, for example, at an angle 2θ of 30°, in prior art approaches the detector may have recorded energy over a broad range, and the output of the experiment would be the energy recorded from 7 keV to above 19 keV. This would accordingly include a large amount of background radiation. In contrast, in the present invention, the range of energy around the output energy that appears in the final output is typically very much less. The reason for this very broad energy range is that the detectors used had very poor resolution.

The X-ray intensity of a peak measured in this way will exclude the contributions from other peaks, since these are fixed, but will nevertheless include a background contribution from the Bragg reflected peak. Thus, to determine the true intensity of an X-ray peak, the X-ray intensity of the Bragg reflected peak slightly above or below the peak measurement energy is measured and subtracted from the intensity of the peak being measured to correct for the background.

For improved accuracy, the X-ray intensity may be measured as a function at energies both above and below the peak energy, where the dominant contribution is the background from the Bragg reflected peak (i.e. the background), and a fitting procedure carried out to estimate the background intensity at the peak which will occur at the location at which the measurement energy and output energy are the same. Conveniently, a linear fit is carried out; alternatively, polynomial or other fits may be carried out instead.

The system in this way may measure close or low energy peaks. For example, the so-called "escape peak" may be measured in the system. Take the element P (phosphorous), closest to Si (silicon, the element used in the detector). The escape peak of P has an energy of 0.3 keV, (2.0 keV minus 1.7 keV), which can be measured by the SDD. Normally, this peak is lost in detector noise at low energies for elements just above the detector element.

To correct for background energy in the measured peak, an embodiment carries out the following steps:

measuring a measured peak X-ray spectrum of the peak having a peak energy;

measuring the X-ray spectrum of a Bragg-reflected background peak at at least one measurement energy and corresponding output energy, both the measurement energy and output energy being spaced from the peak energy;

using the measured X-ray spectrum of the Bragg-reflected background peak to estimate the X-ray spectrum of the Bragg-reflected background peak at the peak energy; and outputting a corrected peak X-ray intensity of the peak by subtracting the estimated X-ray spectrum of the Bragg-reflected background peak from the measured peak X-ray spectrum.

This may be carried out directly from the data presented in the graph of FIG. 9 where the Bragg-reflected background peak 901 is clearly distinguished as it is the peak that varies in a curve as a function of output and measurement energy. Alternatively, the correction may be made on a simple record of the X-ray intensity in a narrow energy range as the measurement energy and output energy are both scanned in parallel so that the measurement energy equals the output energy and both vary together over the scan.

A further aspect is that the collimators can be tuned at the resolution of the SDD. This allows a larger collimator spacing allowing overlapping peak tails to be separated.

Any filters may also be tuned. In conventional WD-XRF, filters may be used to remove interfering tube lines, to suppress spectral impurities from the tube etc. These filters can be made thinner or even removed.

Note further that although the description describes measuring a narrow range of energy around the output energy, this does not imply that only the narrow range of energy is actually measured and recorded by the SDD. It is indeed convenient to only store the X-ray intensity at the measurement energy to reduce storage space, but in embodiments the X-ray intensity is stored as a function both of energy detected by the SDD and of the measurement energy (or equivalently the angle 2θ). FIG. 9 illustrates measurements taken in this way.

The extra information about the intensity of other scattered peaks recorded in this way may provide additional information about the composition of the sample.

Accordingly, in a further advantageous method of use, the X-ray intensity is measured as a function of energy, and a first output includes the X-ray intensity as a function of the measurement energy, or equivalently 2θ.

Additionally, the X-ray intensity may be measured as a function of 2θ for fixed energies, or more exactly at fixed windows of energy around predetermined additional energies. These additional energies may be the energies corresponding to scattered X-rays (the ZnKα energy for example), or energies corresponding to the contamination peaks. These measurements can be used to reduce the background and improve quantitative analysis.

Figure 2:
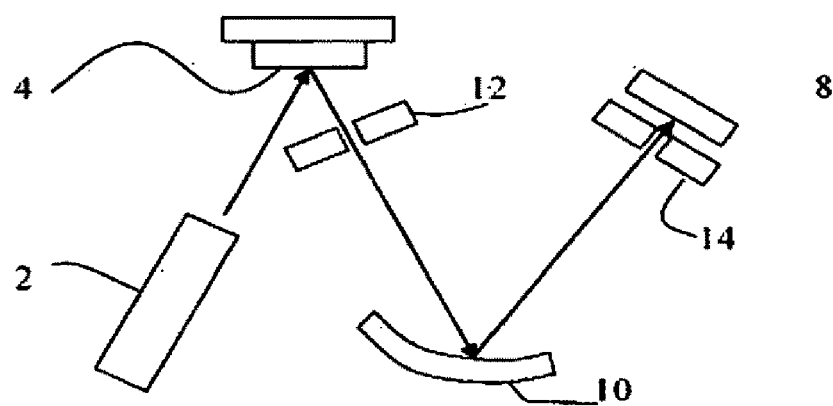
FIG. 2 illustrates an alternative prior art WDXRF apparatus.
Figure 11:
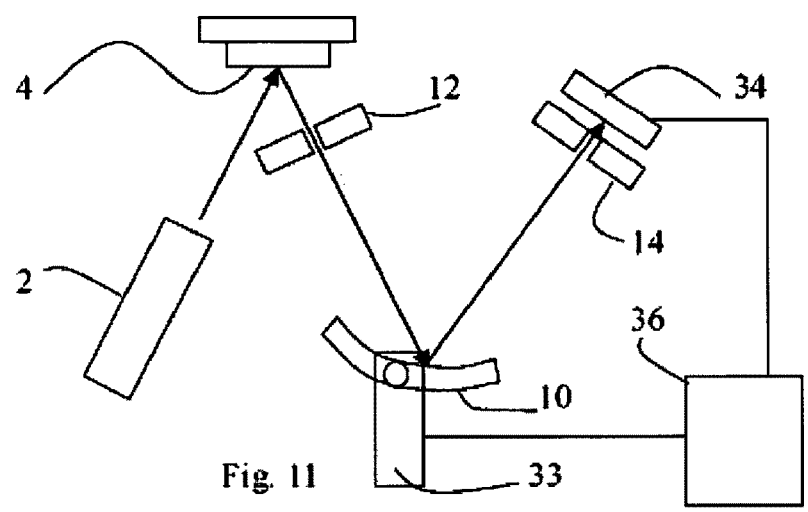
FIG. 11 shows apparatus according to a second embodiment of the invention.

FIG. 11 illustrates a second embodiment according to the invention in which the flat crystal 6 is replaced by a curved crystal 10 and first and second slits. This delivers exactly the same benefits over the prior art of FIG. 2 as the arrangement of FIG. 3 does over the prior art of FIG. 1.

Note that the silicon drift detector 34 needs a more linear array of detector elements to measure X-rays passing through a slit. Thus, for this application, the silicon drift detector 34 may include a line of separate detector elements 38.

The invention may be used over a wide energy range, up to 25 or 30 keV or even more. However, the capture of X-rays by a silicon drift detector becomes less effective at higher energies, say above 15 keV, i.e. a significant fraction of high energy X-rays pass straight through the silicon drift detector and hence are not measured.

Figure 12:
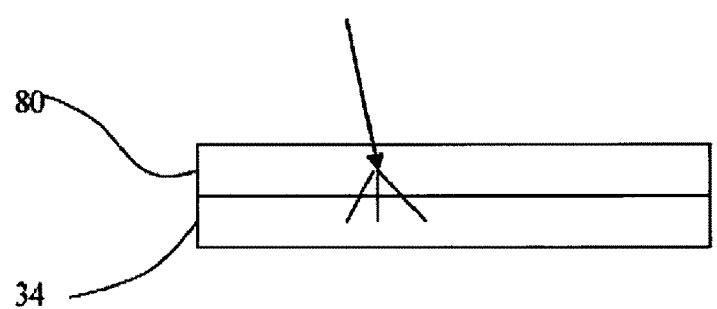
FIG. 12 shows a detector used in a third embodiment of the invention.

Thus, an alternative silicon drift detector that may be used with either the flat or the curved crystal includes a scintillator crystal 80 in front of the silicon drift detector 34 as illustrated in FIG. 12. The scintillator crystal captures X-rays and emits photons at a particular wavelength—the higher the energy of the captured X-rays the greater the number of photons created. These are then captured by the underlying silicon drift detector.

The use of this combination can increase resolution compared with a conventional scintillator which uses a photomultiplier tube, since coupling between the scintillator crystal and silicon drift detector can be good.

The scintillator crystal 80 may be any suitable material, such as NaI, $LaCl_3$ or other materials.

A further embodiment of the invention will now be described with reference to FIGS. 13 to 17. In an embodiment described above, the Bragg background contribution to the peak being measured was corrected by measuring the Bragg background at a different condition, that is a different angle 2θ. In contrast, in another embodiment, the Bragg background is determined by higher order Bragg peaks which may be measured in the same measurement condition, that is the same angle 2θ, but at a different energy.

In particular, there is a relation between the first order Bragg reflected intensity and the higher orders Bragg reflected intensity. Accordingly, the higher order peaks can be used to derive the background intensity at the first order. In practice the second order peak is most suitable to derive the background intensity at the first order, since it is the most intense higher order reflected peak. The scattered tube lines can be used as well but are less intense.

First, a calibration line should be made. The first and second order Bragg reflected intensity should be measured at the 2θ-angle of the element of interest for a representative set of samples. Conveniently, these samples may be standards. These standards should not contain the element of interest, but have representative matrices. The first order intensity is then plotted against the second order intensity for all standards and a calibration line is obtained. This calibration line is then applied each time a sample with the element of interest is analyzed. The analysis should be preferably performed with similar measurement conditions (tube settings, collimator, crystal, detector). The intensity of the second order peak is determined from the measured spectrum, and the background of the first order peak can be directly obtained from the calibration line.

In cases where the matrix effects are constant or can be calculated per sample, two or more standards containing the element of interest in different concentrations can be used for the calibration of the relation between the first and second order Bragg reflected intensity. The reciprocal sensitivity E and the relation r is determined with regression from $C=E*(R_1-r*R_2)*M$ where C is the concentration of the element of interest, $R_1$ and $R_2$ are the $1^{st}$ and $2^{nd}$ order Bragg reflected intensities, and M is the matrix effect.

Another way to determine the background for the first order peak from the higher order reflections is by FP calculations. First a guess of the matrix is made. The corresponding spectrum is simulated and compared to the measured spectrum. This process is iterated several times until the higher orders in the simulated spectrum are in close agreement to these in the measured spectrum. Next, the intensity of the $1^{st}$ order can be directly obtained from the simulated spectrum.

A straightforward example using geology standards is given to illustrate the new background method.

The pulse height distributions of five representative geology standards has been measured at the NiKα Bragg angle. These standards cover the range from a very light to a very heavy matrix. The composition of the standards is set out in the following table:

TABLE 1

| Composition geology standards (in %). | | | |
| --- | --- | --- | --- |
| | $Al_2O_3$ | $SiO_2$ | $Fe_2O_3$ |
| BGS_MON (1301) | | 100 | |
| ProTrace00_appl (1302) | 20 | 75 | 5 |
| ProTrace00_dev (1303) | 20 | 70 | 10 |
| TRMAC3 (1304) | | 75 | 25 |
| TRMAC5 (1305) | | | 100 |

Figure 13:
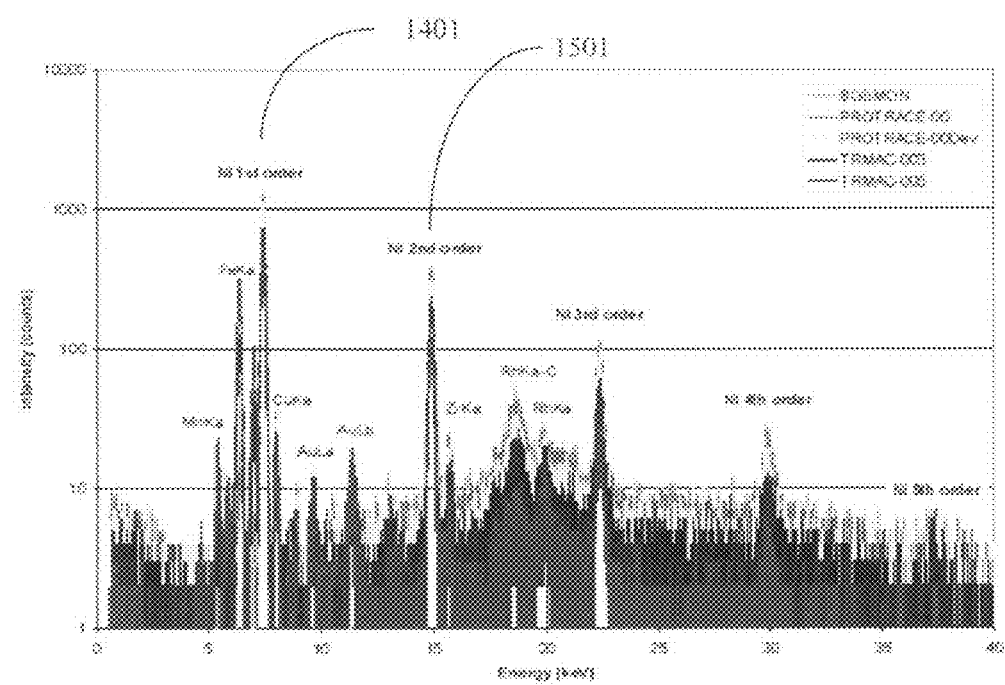
FIG. 13 shows measured spectra for five geology standards at the NiKα Bragg angle ($2\theta=48.67°$)

FIG. 13 shows the spectra measured at the NiKα Bragg angle (2θ=48.67°). The higher order Bragg reflections (up to the $5^{th}$ order!) and the scattered tube lines can be clearly resolved. Furthermore, the peaks are quite intense, especially the second order peak.

Figure 14:
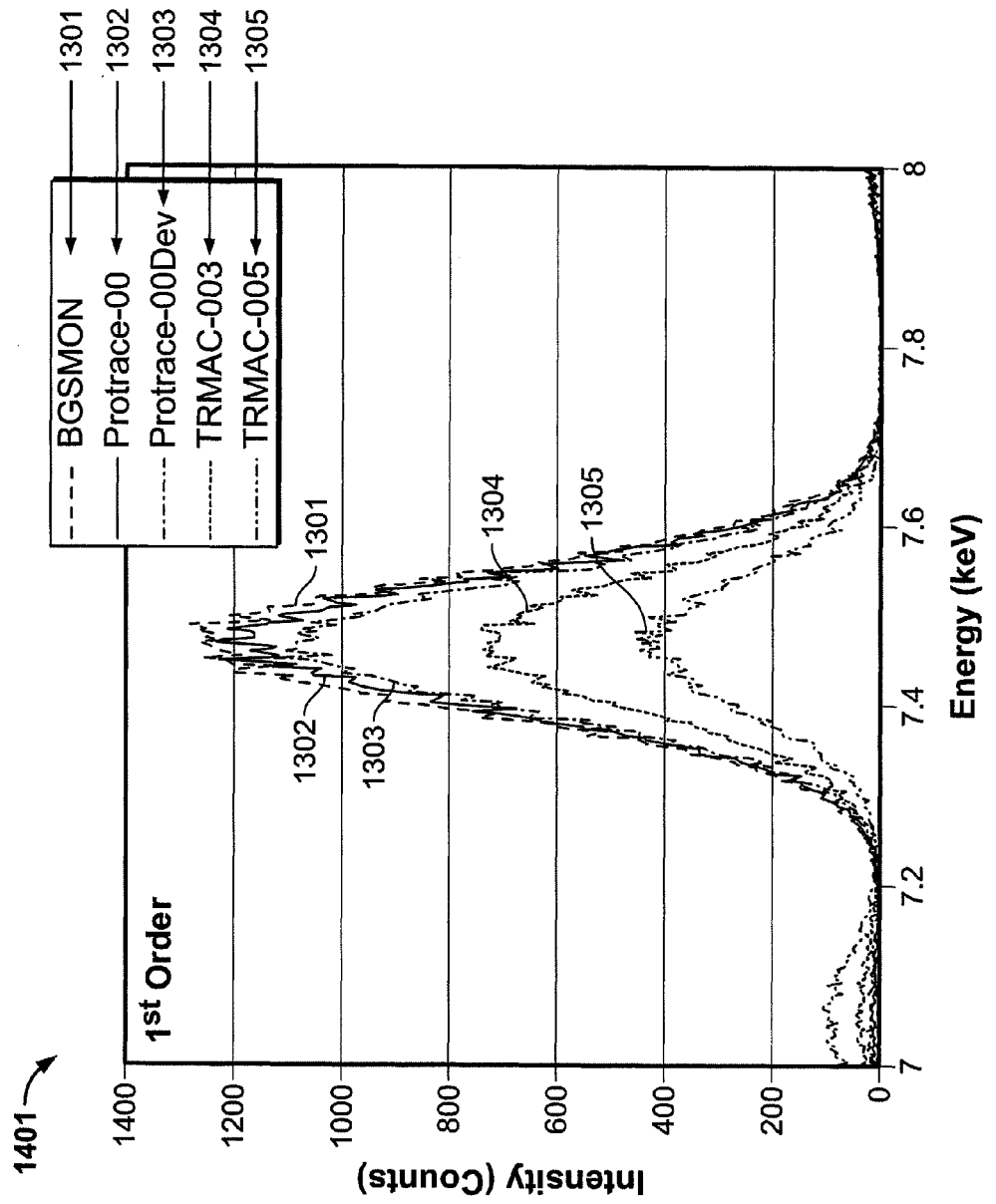
FIG. 14 shows a first order Bragg reflection measured at the NiKα Bragg angle ($2\theta=48.67°$)
Figure 15:
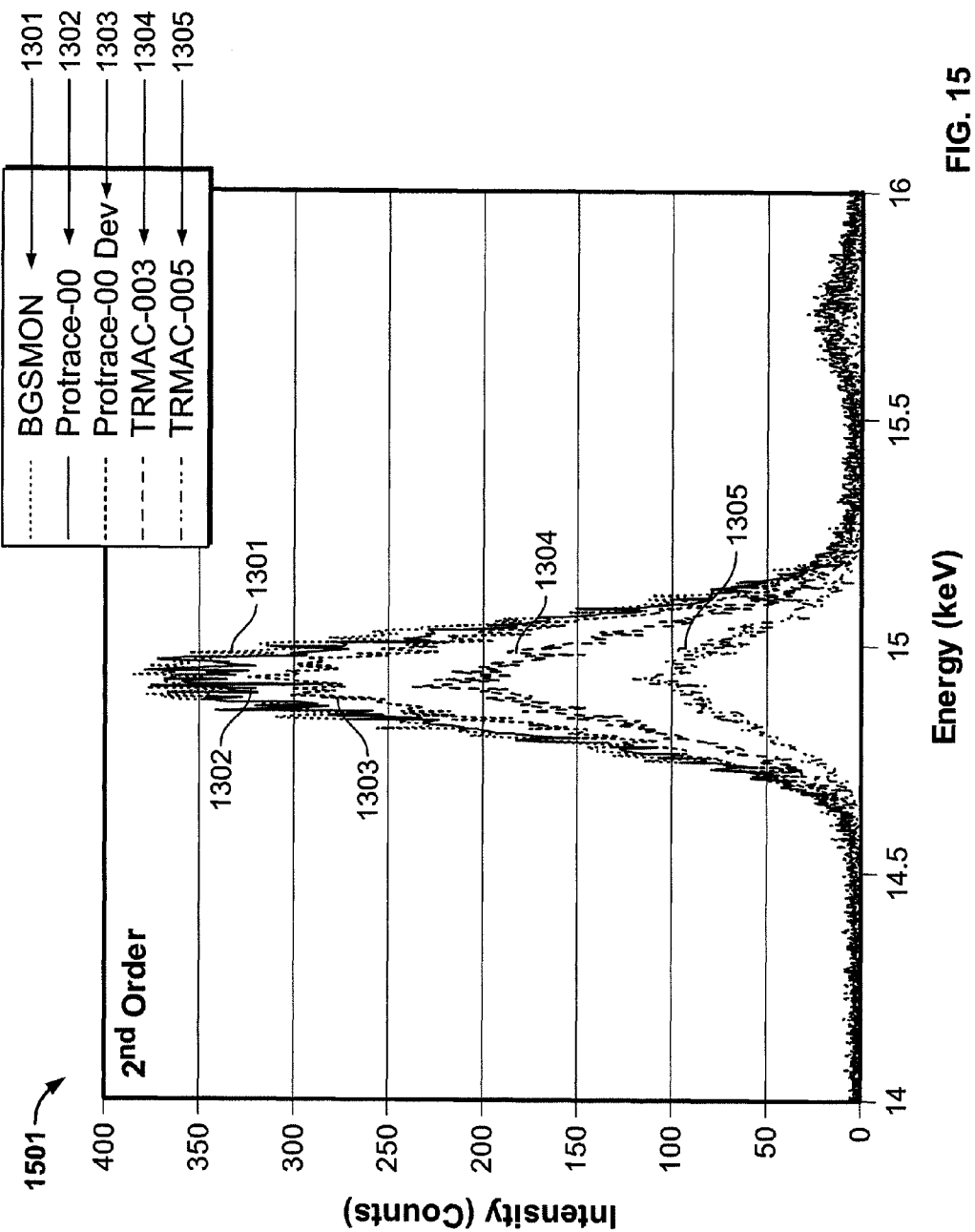
FIG. 15 shows a second order Bragg reflection measured at the NiKα Bragg angle ($2\theta=48.67°$)

In FIGS. 14 and 15 the first order 1401 and second order 1501 reflected peaks are shown (enlargement of FIG. 13). The arrangement of the peaks is in agreement with their mass absorption coefficient (mac).

Figure 16:
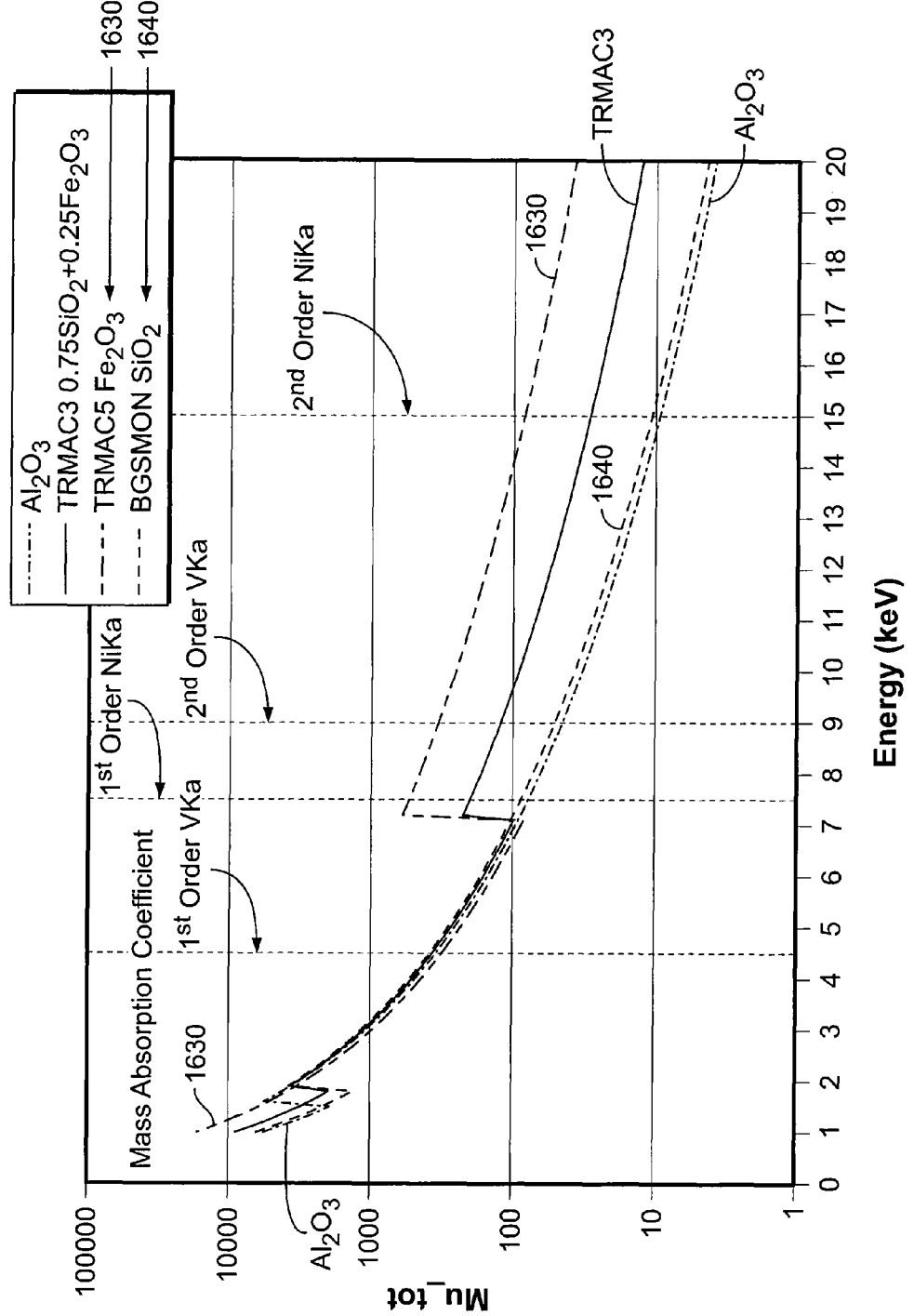
FIG. 16 shows mass absorption coefficients as function of energy for three geology standards.

In FIG. 16 the mass absorption coefficients are shown as function of energy for five geology standards. The lightest matrix (with the lowest mass absorption coefficient: BGS_MON at $1^{st}$ order) yields the highest scattered intensity 1640 and the heaviest matrix (with the highest mass absorption coefficient: TRMAC5) yields the lowest scattered peak 1630. The arrangement of the mass absorption coefficients is the same for both the first order and second order Bragg reflection. Thus the arrangement of the peak intensities is similar for the first and second order reflection, see FIG. 14.

Figure 17:
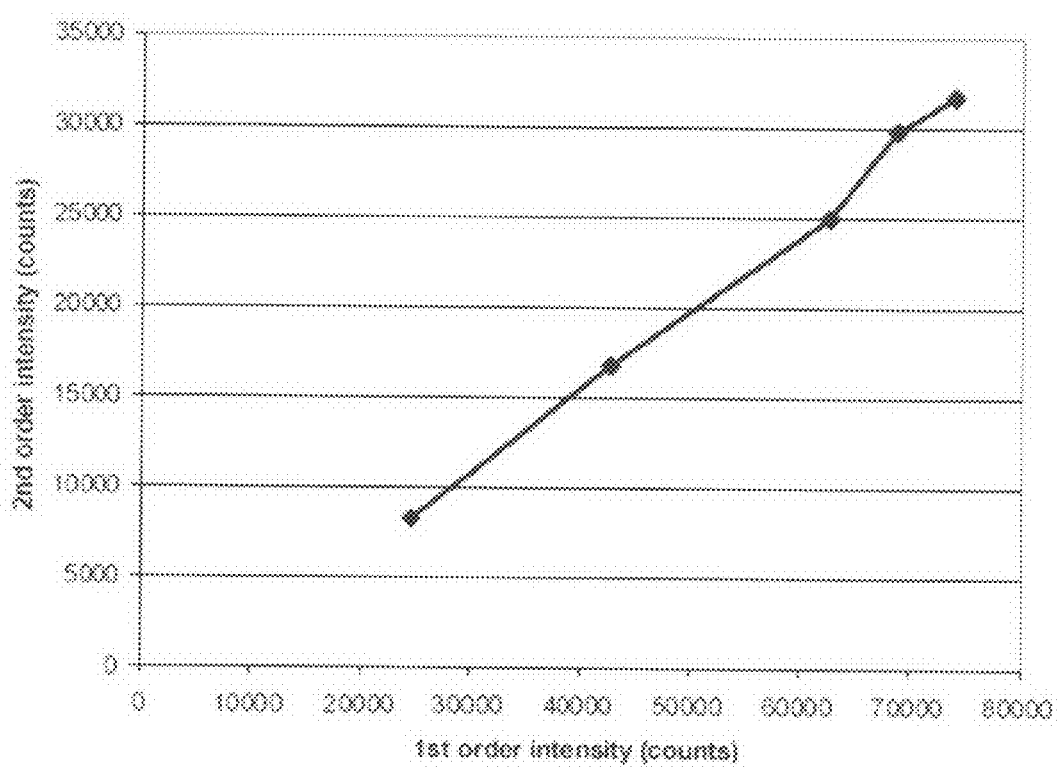
FIG. 17 shows the intensity of the $1^{st}$ order versus $2^{nd}$ order Bragg reflected peak at the NiKα Bragg angle ($2\theta=48.67°$) for three calibration line geology standards.

In FIG. 17 the intensity of the first order Bragg reflected peak is plotted against the intensity of the second order Bragg reflected peak. A nearly linear calibration line is obtained in this case. This calibration line can be applied each time a sample with the element of interest is analyzed. The intensity of the second order peak is determined and the background of the first order peak can be directly obtained from the calibration line.

The relationship is less straightforward when one or more absorption edges are present between the first and second order reflection (see FIG. 16, e.g. Vanadium first and second order), since the arrangement of the peaks is changed. Again a calibration line can be made, but also FP calculations can be performed in order to simulate the background intensity at the $1^{st}$ order peak.

In this way, no background channel is required and measurement time can be significantly reduced. The peak of interest is measured and the correction for Bragg background determined from higher energy peaks that can be measured at the same time. The use of a silicon drift detector allows such higher energy peaks to be measured with sufficient resolution to obtain good results.

The skilled person will realise that modifications and additions can be made to the embodiments described above. For example, the apparatus may in practice include additional components such as X-ray shielding, a vacuum housing, airlocks to introduce samples, equipment to pick and place samples for measurement and the like.

The XRF apparatus may include a number of different detectors. For example, the apparatus can include the detector 34 without the scintillator and a further detector with scintillator crystal to deal with multiple different energies. The desired detector can be moved into place for the required application.

Further, although in the embodiments the analyzer crystal rotates, those skilled in the art will appreciate that it is the relative locations of the various components that gives rise to the measurements, and so various different motions of the sample, detector, analyzer crystal, X-ray source and collimators are possible to carry out the measurements.

The detector need not be a silicon drift detector, but may also be another solid state detector with reasonable resolution, especially semiconductor detectors, capable of detecting X-ray intensity as a function of energy may also be used, for example using Ge or other semiconductor materials or a charged coupled device (CCD). Note that the semiconductor detectors need not necessarily use conventional semiconductor materials, but equivalents such as semiconducting polymers and similar materials may also be used.

The resolution of the detector should be good enough to resolve the peaks. Thus, the resolution of the detector should preferably be better than the narrow range of energy used over the whole range of measurement so that the resolution of the detector does not dominate the width of the peaks.

Similarly, deconvolution may also be used for the measurement of X-ray intensity at fixed energies.

The control electronics, or processing means, may be any combination of hardware and software as will be appreciated by those skilled in the art.

What is claimed is:

1. An X-ray fluorescence apparatus comprising:
   a sample holder (30) for holding a sample;
   an X-ray source (2) for directing X-rays onto the sample in the sample holder;
   a silicon drift detector (8) for detecting X-ray intensity as a function of energy;
   an analyzer crystal (6,10) for directing X-rays from the sample onto the detector (8);
   a processor arranged to take a signal from the detector (8) and to output a processed X-ray intensity; and
   a driver for varying a configuration of at least one of the sample, the source, the analyzer crystal or the detector to select a measurement energy at which X-rays from the sample are directed by the analyzer crystal onto the detector;
   wherein the processor is arranged to output an X-ray spectrum of a peak at a peak energy, by:
   measuring a measured X-ray spectrum of the peak;
   measuring an X-ray spectrum of a Bragg-reflected background peak at least one measurement energy and output energy, the measurement energy and output energy being the same energy spaced from the peak energy;
   using the measured X-ray spectrum of the Bragg-reflected background peak to estimate an X-ray spectrum of the Bragg-reflected background peak at the peak energy; and
   outputting a corrected peak X-ray intensity of the peak by subtracting the estimated X-ray spectrum of the Bragg-reflected background peak from the measured X-ray spectrum of the peak.

2. The X-ray fluorescence apparatus of claim 1, wherein the detector (8) is a multi-segment silicon drift detector (34).

3. The X-ray fluorescence apparatus of claim 1, wherein the detector (8) includes a scintillator crystal (80) mounted on the detector (34).

4. The X-ray fluorescence apparatus of claim 1, wherein the driver includes control electronics (36) and a drive (33) adapted to rotate the crystal (6) to scan the measurement energy.

5. An X-ray fluorescence apparatus comprising:
   a sample holder (30) for holding a sample;
   an X-ray source (2) for directing X-rays onto the sample in the sample holder;
   a silicon drift detector (8) for detecting X-ray intensity as a function of energy;
   an analyzer crystal (6,10) for directing X-rays from the sample onto the detector (8);
   a processor arranged to take a signal from the detector (8) and to output a processed X-ray intensity; and
   a driver for varying a configuration of at least one of the sample, the source, the analyzer crystal or the detector to select a measurement energy at which X-rays from the sample are directed by the analyzer crystal onto the detector;
   wherein the processor is arranged to output an X-ray spectrum of a peak at a peak energy, by:
   measuring a measured X-ray spectrum of the peak;
   measuring an X-ray spectrum of a higher order Bragg-reflected background peak or scattered tube lines;
   using the measured X-ray spectrum of the higher order Bragg-reflected background peak or scattered tube lines to estimate an X-ray spectrum of the Bragg-reflected background peak at the peak energy; and
   outputting a corrected peak X-ray intensity of the peak by subtracting the estimated X-ray spectrum of the Bragg-reflected background peak from the measured X-ray spectrum of the peak.

6. The X-ray fluorescence apparatus of claim 5, wherein the detector (8) is a multi-segment silicon drift detector (34).

7. The X-ray fluorescence apparatus of claim 5, wherein the detector (8) includes a scintillator crystal (80) mounted on the detector (34).

8. The X-ray fluorescence apparatus of claim 5, wherein the driver includes control electronics (36) and a drive (33) adapted to rotate the crystal (6) to scan the measurement energy.

9. A method of carrying out X-ray fluorescence measurements, comprising:
   directing X-rays onto a sample;
   measuring an intensity of X-rays incident on a detector as a function of energy;
   directing X-rays emitted by the sample off an analyzer crystal (6) onto the detector (8);
   varying the configuration of the sample, a source, the analyzer crystal, or the detector to select a measurement energy at which X-rays from the sample are directed by the analyzer crystal onto the detector;
   selecting X-rays in a narrow energy range around an output energy and outputting the intensity of X-rays in the narrow energy range, the narrow energy range having a width less than 0.4 keV for an output energy below 1 keV, a width less than 1 keV for an output energy from 1 keV to 5 keV, a width less than 2 keV for an output energy from 5 keV to 10 keV, or a width less than 5 keV for an output energy above 10 keV; and
   calculating an intensity of a peak at a peak energy, by:
   measuring a measured X-ray spectrum of the peak;
   measuring an X-ray spectrum of a Bragg-reflected background peak at least one measurement energy and output energy, the measurement energy and output energy being the same energy spaced from the peak energy;
   using the measured X-ray spectrum of the Bragg-reflected background peak to estimate an X-ray spectrum of the Bragg-reflected background peak at the peak energy; and
   outputting a corrected peak X-ray intensity of the peak by subtracting the estimated X-ray spectrum of the Bragg-reflected background peak from the measured X-ray spectrum of the peak.

10. The method according to claim 9, wherein varying the configuration includes rotating the analyzer crystal and detector (8).

11. The method according to claim 9, wherein as the measurement energy varies, the output energy varies to stay the same as the measurement energy.

12. The method according to claim 9, further comprising additionally outputting the measured X-ray intensity at predetermined fixed output energies as the measurement energy varies.

13. The method according to claim 9, further comprising outputting the X-ray intensity as three dimensional plot as a function of measurement energy and of the output energy.

14. The method according to claim 9, wherein:
the step of measuring the intensity of X-rays includes outputting from the detector the measured X-ray intensity as a function of energy to a processor (36); and
the step of selecting X-rays in a narrow energy range includes selecting the narrow energy range in the processor (36).

15. A method of carrying out X-ray fluorescence measurements, comprising:
directing X-rays onto a sample;
measuring an intensity of X-rays incident on a detector as a function of energy;
directing X-rays emitted by the sample off an analyzer crystal (6) onto the detector (8);
varying the configuration of the sample, a source, the analyzer crystal, or the detector to select a measurement energy at which X-rays from the sample are directed by the analyzer crystal onto the detector;
selecting X-rays in a narrow energy range around an output energy and outputting the intensity of X-rays in the narrow energy range, the narrow energy range having a width less than 0.4 keV for an output energy below 1 keV, a width less than 1 keV for an output energy from 1 keV to 5 keV, a width less than 2 keV for an output energy from 5 keV to 10 keV, or a width less than 5 keV for an output energy above 10 keV; and
calculating an intensity of a peak at a peak energy, by:
measuring a measured X-ray spectrum of the peak;
measuring an X-ray spectrum of a higher order Bragg-reflected background peak or scattered tube lines;
using the measured X-ray spectrum of the higher order Bragg-reflected background peak or scattered tube lines to estimate an X-ray spectrum of the Bragg-reflected background peak at the peak energy; and
outputting a corrected peak X-ray intensity of the peak by subtracting the estimated X-ray spectrum of the Bragg-reflected background peak from the measured X-ray spectrum of the peak.

16. The method according to claim 15, wherein varying the configuration includes rotating the analyzer crystal and detector (8).

17. The method according to claim 15, wherein as the measurement energy varies, the output energy varies to stay the same as the measurement energy.

18. The method according to claim 15, further comprising additionally outputting the measured X-ray intensity at predetermined fixed output energies as the measurement energy varies.

19. The method according to claim 15, further comprising outputting the X-ray intensity as three dimensional plot as a function of measurement energy and of the output energy.

20. The method according to claim 15, wherein:
the step of measuring the intensity of X-rays includes outputting from the detector the measured X-ray intensity as a function of energy to a processor (36); and
the step of selecting X-rays in a narrow energy range includes selecting the narrow energy range in the processor (36).

* * * * *